United States Patent [19]

Myers

[11] Patent Number: 5,304,199
[45] Date of Patent: Apr. 19, 1994

[54] APPARATUS FOR ARTERIAL TOTAL OCCLUSION PLAQUE SEPARATION

[75] Inventor: Gene E. Myers, Sarasota, Fla.

[73] Assignee: Gene E. Myers Enterprises, Inc., Sarasota, Fla.

[21] Appl. No.: 822

[22] Filed: Jan. 4, 1993

[51] Int. Cl.⁵ ............................................. A61M 29/02
[52] U.S. Cl. .................................................. 606/194
[58] Field of Search .................. 606/192, 194, 196; 604/96

[56] References Cited

U.S. PATENT DOCUMENTS

| | | |
|---|---|---|
| 4,351,341 | 9/1982 | Goldberg et al. . |
| 4,364,394 | 12/1982 | Wilkinson . |
| 4,413,989 | 11/1983 | Schjeldahl et al. ............. 604/104 X |
| 4,575,371 | 3/1986 | Nordquist et al. . |
| 4,684,363 | 8/1987 | Ari et al. .......................... 604/104 X |
| 4,762,129 | 8/1988 | Bonzel .............................. 604/96 X |
| 4,781,681 | 11/1988 | Sharrow et al. . |
| 4,832,691 | 5/1989 | Witzel .............................. 606/192 X |
| 4,886,059 | 12/1989 | Weber . |
| 4,921,478 | 5/1990 | Solano et al. ...................... 604/96 X |
| 4,994,032 | 2/1991 | Sugiyama et al. .................. 604/96 |

FOREIGN PATENT DOCUMENTS 0351734 1/1990 European Pat. Off. ............. 604/96

Primary Examiner—Michael H. Thaler
Attorney, Agent, or Firm—Patterson & Keough

[57] ABSTRACT

A method for surgically enlarging an arterial lumen totally occluded by a stenotic lesion, and a unique balloon catheter used during that operation. The balloon catheter is generally rod shaped and includes an elongated tubular member having a double central lumen with a proximal end and a distal end and a balloon portion having a concave distal tip smaller in diameter than the proximal tip. The method takes advantage of the catheter design and includes positioning of the catheter in close proximity to a total occlusion and inflating the balloon to form a plaque cleft.

6 Claims, 5 Drawing Sheets

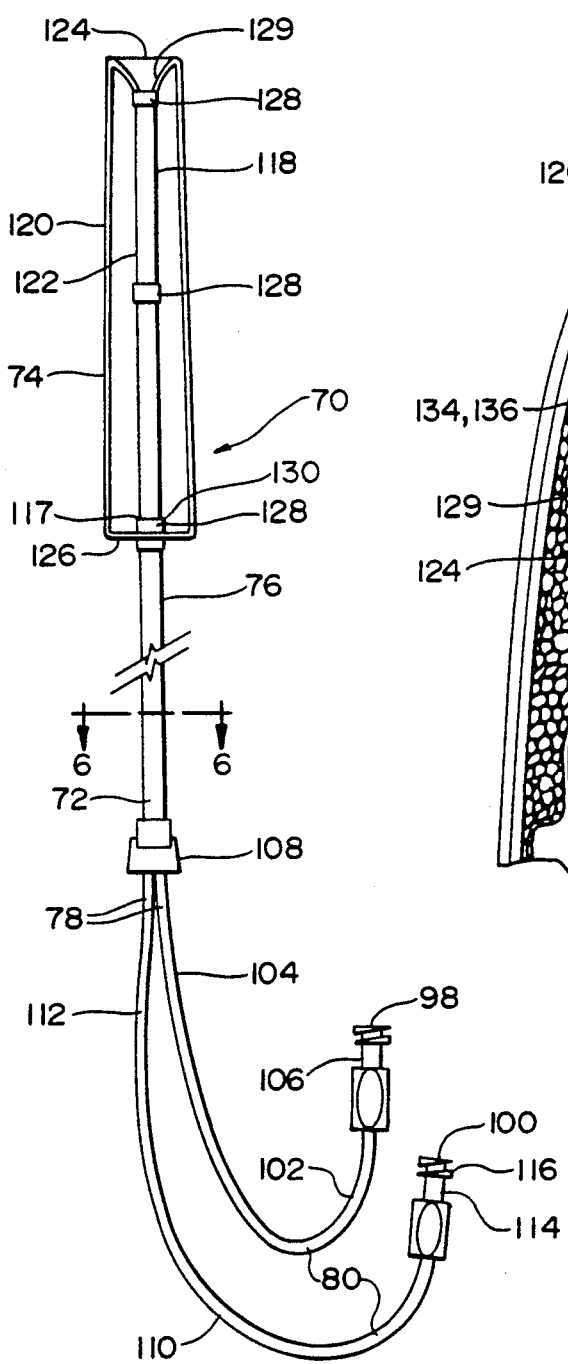
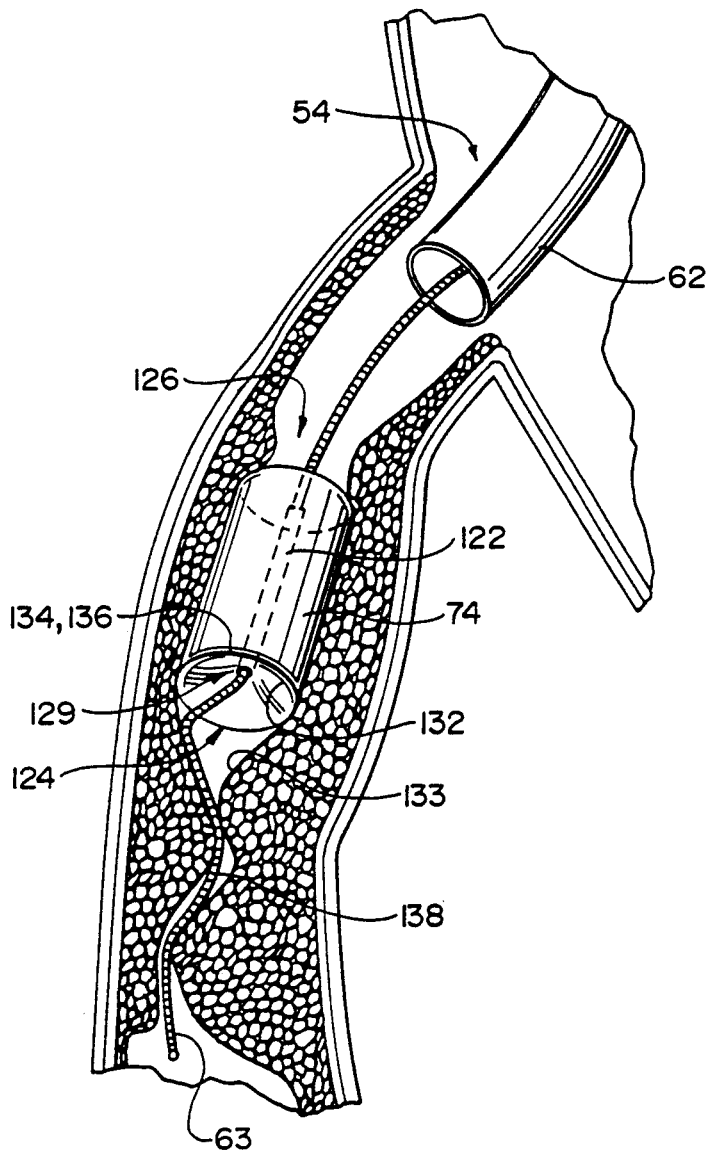
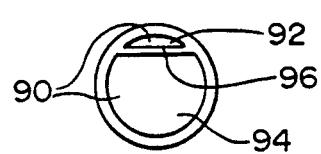

APPARATUS FOR ARTERIAL TOTAL OCCLUSION PLAQUE SEPARATION

TECHNICAL FIELD

The invention relates generally to the field of angioplasty, the non-surgical reconstruction of a blood vessel. In particular, it relates to a method and apparatus for percutaneous transluminal angioplasty, that is non-surgically enlarging an arterial lumen totally occluded by a stenotic lesion, and to a unique catheter used during that operation.

BACKGROUND OF THE INVENTION

Atherosclerosis is a disease that is characterized by irregularly distributed lipid deposits, called plaque. Plaque is deposited in the lumen or central portion of large and medium-sized arteries and results in a narrowing of the lumen. Atherosclerosis usually occurs in the second or third decade of life and typically affects the entire length of the coronary artery in varying degrees. In some portions of the coronary artery, the arterial lumen exhibits a more severe narrowing called "stenosis." When the stenosis severity reaches across 75–80% of the cross sectional area of the artery, symptoms of myocardial ischemia, the inadequate circulation of blood to the myocardium, the muscular layer of the heart, occur. Myocardial ischemia is sometimes accompanied by angina pectoris, a severe constricting pain in the chest radiating from the chest into the shoulder and down the left arm. Also attendant with the progression from stenosis to total occlusion of the coronary artery are coronary spasms and the formation of intraluminal coronary thrombi or blood clots.

Plaque consists of acellular fibrous tissue, calcified tissue and amorphous debris that includes cholesterol clefts containing extra-cellular lipid, called pultaceous debris. It is known that plaque morphology varies as a function of cross-sectional narrowing of the artery. That is, the amount of plaque increases as the severity of stenosis increases and at times, produces total occlusion of the coronary artery that requires reconstructive revascularization by the traditional method called coronary transluminal angioplasty.

Percutaneous transluminal coronary angioplasty (PTCA), using a balloon catheter was first introduced in the mid-1970's and has become one of the recognized methods for treating obstructed coronary arteries. The procedure is generally performed by making a needle puncture in the patient's groin to gain access to the femoral artery and a sheath or introducer is inserted into the wound. A guidewire is passed through the sheath and routed through the vascular system until the distal end of the wire reaches the coronary ostium, the opening from the ascending aorta into the coronary artery. A guiding catheter is next advanced over the guidewire until its distal end exits over the distal end of the guidewire. A special PTCA wire is then advanced through the guiding catheter into the proximal coronary stump, the area between the ostium and the occlusion, up to the origin of the total occlusion. The physician, by manipulating the proximal end of the wire, attempts to pass it across the stenotic lesion that is obstructing the artery. If the physician successfully manipulates the guidewire past the stenotic lesion, a PTCA balloon angioplasty catheter is passed over the guidewire by feeding the distal end of the balloon catheter over the proximal end of the guidewire and then pushing the balloon catheter over the guidewire until the balloon is adjacent to the stenotic lesion. In position, the balloon is inflated to press the occlusion against the wall of the artery thus restoring patency to the artery.

Frequently, however, the traditional method of transluminal angioplasty using a balloon catheter is not successful because it depends on the ability to insert the guidewire through the stenosis. If the stenosis is so dense that the guidewire cannot be inserted through it, the balloon catheter will also not be able to pass through the stenosis. Rather, the balloon can only be advanced up to the tip of the wire, just outside the occlusion, and then inflated. In this case arterial patency will not be restored.

Another problem associated with the traditional method is due to the fact that total occlusions frequently occur very close to the ostium. Thus, a very short area in which the physician may manipulate the balloon is provided (the "coronary stump"). PTCA balloons are commercially available in lengths of at least two centimeters. If the balloon is inflated in a coronary stump of less than two centimeters, it may displace the guiding catheter away from the occlusion and into the arterial wall and the balloon may tear.

In addition, conventional balloon catheters have tapered oval ends with a shaft tip extending three to five millimeters beyond the distal portion of the balloon. If the physician is unable to direct the shaft tip to the ideal location relative to the total occlusion, the tip may bend thereby reducing the extent to which the physician may advance it further into the artery. Furthermore, the shaft tip prevents the balloon from entering the most proximal portion of the total occlusion. If the balloon cannot enter the occlusion, it cannot be inflated directly adjacent to the total occlusion. This reduces the chances of restoring patency to the totally occluded artery.

A tapered balloon has the added undesirable effect of allowing the arterial wall in the area adjacent to the total occlusion to recoil, which prevents the development of a cleft. Cleft formation during percutaneous transluminal angioplasty is desirable because it provides the pathway through which the guidewire may be inserted across the total occlusion. This in turn enhances the successful completion of the procedure.

The success rate of the conventional method is further mitigated by abrupt total occlusion of the artery without tapering, total occlusion of the artery of greater than six months duration, stenotic lesions greater than three centimeters in diameter, and occlusion that is flush at the ostium of the vessel that allows no stump with which to start the procedure.

Objects and advantages of the present invention in achieving these and other goals will become apparent from the following descriptions, taken in connection with the accompanying drawings, wherein are set forth by way of illustration and example certain embodiments of the present invention.

SUMMARY OF THE INVENTION

The problems outlined above that have inhibited successful percutaneous transluminal angioplasty are in large measure solved by the balloon catheter method of percutaneous transluminal angioplasty in accordance with the present invention. The method of percutaneous transluminal angioplasty in accordance with the present invention enables the use of a unique catheter that permits the separation of the arterial wall adjacent to a total occlusion thus forming a "cleft." The formation of a cleft permits the angioplasty wire to readily cross the total occlusion resulting in successful percutaneous transluminal angioplasty.

The balloon and catheter in accordance with the present invention consists of three complimentary members, a guiding catheter, a guidewire and a balloon catheter. The guiding catheter and guidewire are conventional. The balloon catheter is generally rod shaped and includes, an elongated tubular member having a double central lumen with a proximal end and a distal end and a balloon portion having a concave distal tip smaller in diameter than the proximal tip. The balloon catheter in accordance with the present invention is especially designed for percutaneous transluminal angioplasty of totally occluded arteries.

Percutaneous transluminal angioplasty in accordance with the present invention is performed by inserting a guidewire into the femoral artery and up through the descending aorta. A conventional guiding catheter is positioned over the guidewire and advanced up to the ostium of the occluded coronary artery. A balloon catheter and PTCA wire are advanced through the guiding catheter and are positioned adjacent to the total occlusion. The balloon is then inflated, a plaque cleft is formed, and the PTCA wire is manipulated to explore the entire surface area of the cleft. Once the wire has crossed the cleft into the distal patent arterial lumen beyond the total occlusion, the balloon is deflated and withdrawn leaving the PTCA wire across the newly developed cleft. Then, conventional angioplasty is commenced.

One of the advantages of the present invention is that the unique shape of the balloon catheter allows the physician to advance the balloon to within one-half a millimeter of a total occlusion. Inflation of the balloon in close proximity to the total occlusion permits the formation of a cleft thereby enhancing the success rate of conventional percutaneous transluminal angioplasty.

The drawings constitute a part of this specification and include exemplary embodiments with the present invention, while illustrating various objects and features thereof. It will be understood that in some instances relative material thicknesses and relative component sizes and dimensions may be shown exaggerated to facilitate an understanding of the invention.

BRIEF DESCRIPTION OF THE DRAWINGS

FIG. 5 is a side elevation view of the balloon catheter configuration according to the present invention;

FIG. 6 is a cross section of the shaft illustrating the balloon inflation lumen and wire lumen according to the present invention;

FIG. 7 is a view similar to that of FIG. 2 illustrating a balloon catheter in accordance with the present invention as it may be disposed during a percutaneous transluminal angioplasty procedure;

As required, detailed embodiments of the present invention are disclosed herein. It is to be understood, however, that the disclosed embodiments are merely exemplary of the invention, which may be embodied in various forms. Therefore, specific structural and functional details herein are not to be interpreted as limiting, but rather as a basis for the claims and as a representative basis for teaching one skilled in the art to variously employ the present invention in virtually any appropriately detailed system or structure.

DETAILED DESCRIPTION OF THE DRAWINGS

Figure 1:
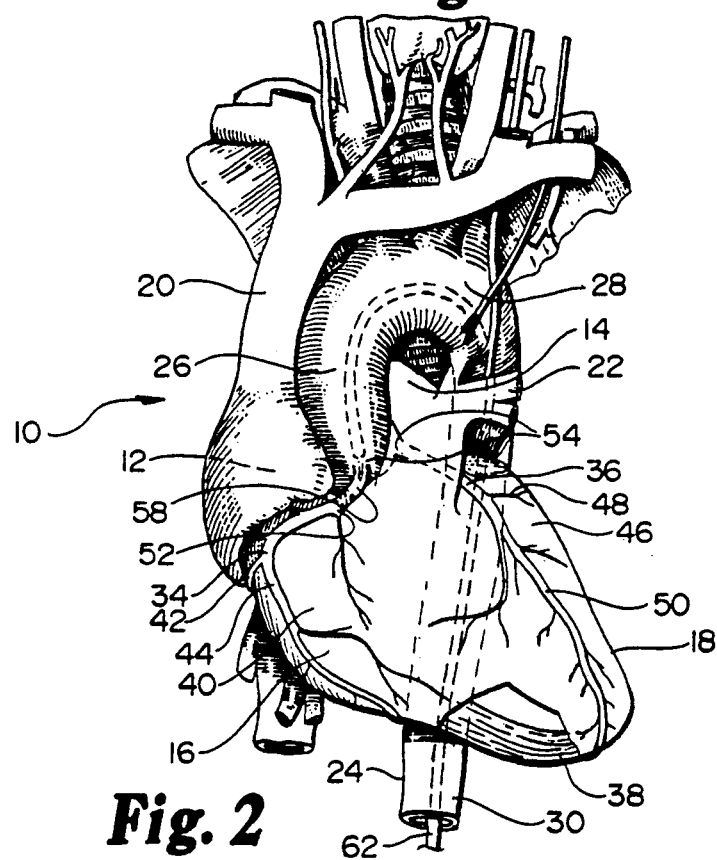
FIG. 1 is an anterior pictorial view of the heart with a partial cross sectional view of the ascending and descending aorta illustrating a totally occluded coronary artery and the placement of the present invention through the aorta.

FIG. 1 depicts a human heart 10. The heart 10 is the bodily organ that pumps blood throughout the body. The interior of the heart 10 is divided into four compartments, two upper atriums 12, 14 and two lower ventricles 16, 18. Blood is pumped into the right atrium 12 of the heart 10 via the vena cave 20. It travels into the right ventricle 16 and is then forced into the pulmonary artery 22 which takes it to the lungs (not shown) where it is oxygenated. From the lungs, the blood flows to and enters the left atrium 14. From there it passes into the left ventricle 18. When the left ventricle 18 contracts, the blood is driven out into the aorta 24 and is circulated throughout the body to supply oxygen to other parts of the body.

The aorta 24 is a large artery that is divided into three parts, the ascending aorta 26, the aortic arch 28 and the descending aorta 30. The descending aorta 30 stems through the central trunk of the body and branches into the femoral artery (not shown), which supplies oxygenated blood to the legs. The ascending aorta 26 branches into the right coronary artery 34 and the left coronary artery 36. The right and left coronary arteries 34, 36 surround the heart 10 and supply blood to its muscular walls, the myocardium 38. The right coronary artery 34 supplies oxygenated blood to the muscle wall 40 of the right ventricle 16. The right coronary artery 34 branches into several descending branches 42, 44. The left coronary artery 36 supplies oxygenated blood to the muscle wall 46 of the left ventricle 18 and divides into two branches, the circumflex artery 48 and the anterior descending branch 50.

A total plaque occlusion 52 may occur in either the right 34 or left 36 coronary artery but frequently occurs within 10 to 20 millimeters of the coronary ostium 54. The area located between the origin of the coronary ostium 54 and the total occlusion 52 is called the right or left coronary artery "stump" 58. Partial plaque occlusions 52 can be successfully treated by a non-surgical procedure such as percutaneous transluminal angioplasty. If not treated, a partial occlusion may develop into a total occlusion 52 which can result in myocardial infarction, and permanent irreplaceable injury to the myocardium. Natural bypasses may occur, however, allowing the preservation of the myocardium notwithstanding the existence of a totally occluded coronary artery. In the setting of a totally occluded coronary artery serving functional myocardium, resultant myocardial ischemia may necessitate revascularization to relieve symptoms or prevent death.

Figure 2:
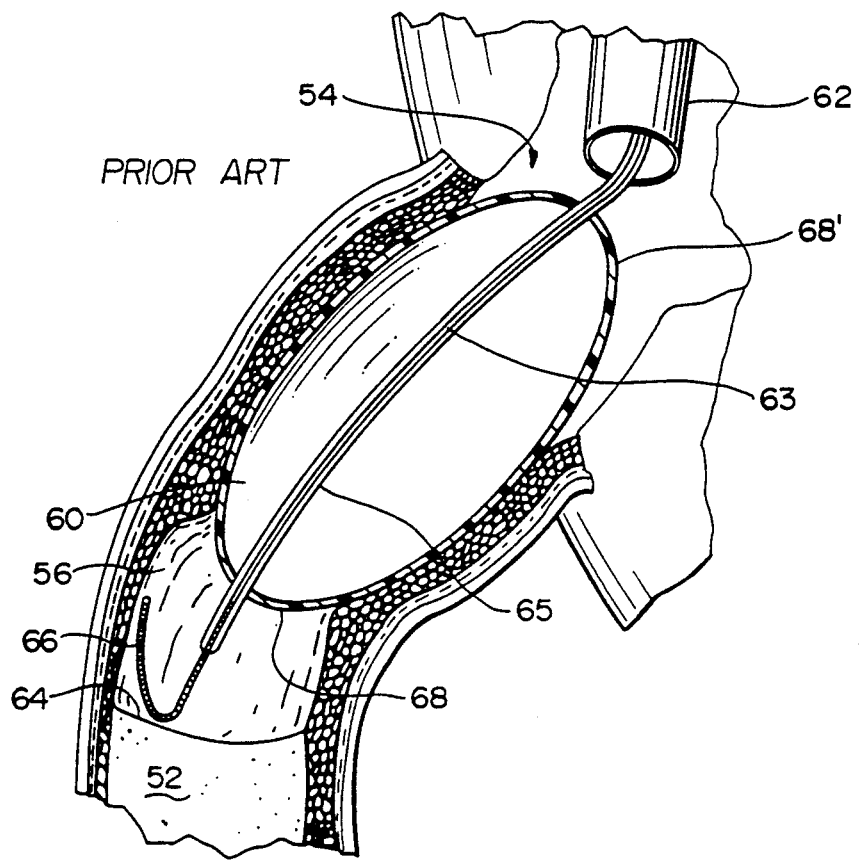
FIG. 2 is a side sectional view of a prior art balloon catheter in use, with anatomical parts cut away.
Figure 2A:
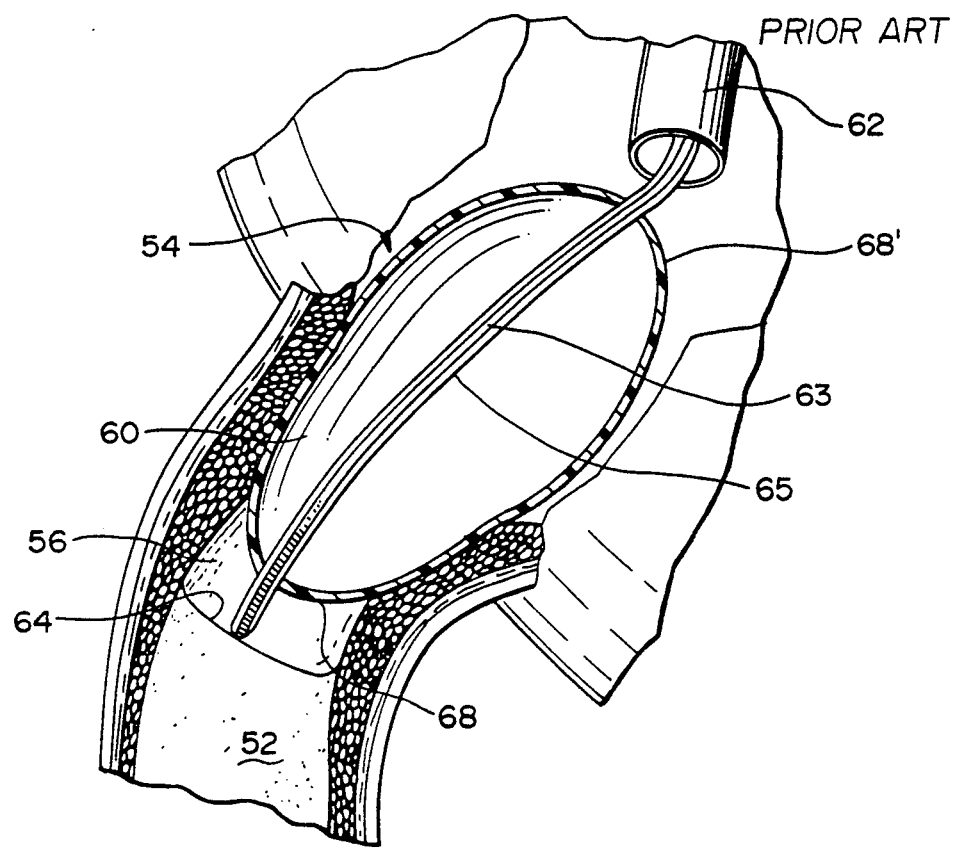
FIG. 2a is similar to FIG. 2, but depicts the problems associated with using a prior art balloon catheter to treat a coronary artery having an occlusion in close proximity to the coronary ostium.

FIGS. 2, 2a, 3, and 4 depict the balloon catheter 60 used in conventional percutaneous transluminal angioplasty. In the prior art method, a needle puncture is made in the patient's groin to gain access to the femoral artery. A guidewire (not shown) is passed through the femoral artery, up the descending aorta 30 until it reaches the coronary ostium 54. A guiding catheter 62 is advanced over the guidewire until it exits over the distal end of the guidewire adjacent to the coronary ostium 54. The guidewire is removed and a PTCA wire 63 is advanced through the guiding catheter 62 into the coronary stump 56 up to the origin 64 of the total occlusion 52. If the physician successfully manipulates the PTCA wire 63 past the total occlusion 52, the prior art balloon catheter 60 may be passed over the PTCA wire 63 and conventional transluminal angioplasty carried out. If the PTCA wire 63 cannot be manipulated across the total occlusion 52, the balloon catheter shaft 65 is advanced up to the tip of the wire 63 and inflated. This often results in displacement of the guiding catheter 62 rearwardly of the ostium presenting the possibility that the balloon will be torn by the head of the guiding catheter 62. Moreover, referring to FIG. 2a, when the occlusion is in close proximity to the coronary ostium, the balloon cannot fully enter the artery and inflation of the artery will cause the sloped forward portion of the balloon to engage the artery sidewall. Expulsion of the balloon from the artery may result. Moreover, as can be seen in FIGS. 2 and 2a, the tip of wire 63 extends beyond the forward end wall of the balloon, preventing balloon expansion directly adjacent to the total occlusion 52. This in turn inhibits and often prevents the formation of a cleft through which the PTCA wire 63 may be passed. For the above reasons, a total occlusion is not in all instances treatable with conventional balloon catheters, leaving surgical bypass as the only treatment option available.

FIGS. 5, 6, 7, 8, 9, and 10 depict the balloon catheter 70 in accordance with the present invention. Balloon catheter 70 broadly includes an elongated flexible tubular member 72 and balloon member 74. The generally rod-shaped tubular member 72 includes shank 76, bifurcated distal end 78 and bifurcated proximal end 80. The generally rod shaped elongated central shank 76 includes a central lumen 90 consisting of an upper balloon inflation lumen 92 and a lower wire lumen 94. The two lumens are separated by a lumen wall 96 that extends along the horizontal axis of the tubular member 72. The central shank 76 may be made from any number of medical grade plastics used in the manufacture of intravascular catheters including, by way of example, polyurethane, polyethylene, tetrafluoroethylene fluorocarbon polymer, nylon or other suitable materials.

Bifurcated proximal end 80 includes PTCA wire port 98 and balloon inflation port 100. PTCA wire port 98 includes a generally elongated hollow cylindrical shaft 102, first wire port end 104 and second wire port end 106. The first end of PTCA wire port 104 is connected to lower wire lumen 94 at junction member 108. Hollow shaft 102 provides means for introducing PTCA wire 63 through shank 76.

Balloon inflation port 100 includes a generally elongated hollow cylindrical stem 110, first balloon port end 112 and second balloon port end 114. Balloon inflation port first end 112 is connected to balloon inflation lumen 92 at junction member 108. Second balloon inflation port end 114 includes a connector mechanism 116, well-known in the prior art, for connecting stem 110 to a conventional air source (not shown). Hollow stem 110 provides the pathway for introducing air into balloon inflation lumen 92, which in turn introduces balloon inflation air into balloon member 74 at balloon inflation lumen outlet 117. The precise location of balloon inflation lumen outlet 117 may vary within the scope of this invention.

Figure 10:
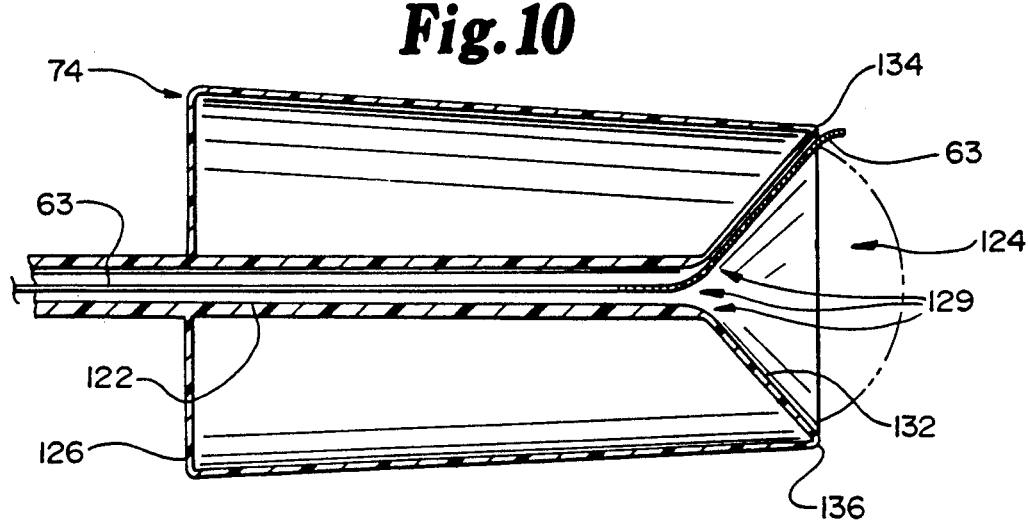
FIG. 10 is a side elevation sectional diagram of the balloon catheter in accordance with the present invention illustrating the range of possible PTCA wire exploration.

Referring particularly to FIGS. 5 and 10, balloon member 74 is generally trapezoidal shaped in longitudinal cross sectional and includes inner surface 118, outer surface 120, hollow chamber member 122, distal portion 124 and proximal portion 126. The outer diameter of balloon 74 is smaller than the inner diameter of guiding catheter 62. Balloon member 74 is preferably made from polyethylene terephthalate or other suitable materials. Balloon member 74 is connected to shank 76 by welding, heat pressing or other suitable means. Inner surface 118 of balloon member 74 contains gold radiopaque markers 128, well-known in the prior art, for monitoring the location of balloon catheter 70. Markers 128 may be alternately located along shaft 76 or hollow chamber member 122.

Inner surface 118 surrounds and is molded to hollow chamber member 122 in an air-tight relationship. Hollow chamber member 122 extends along the longitudinal axis of balloon member 74 from proximal portion 126 to distal portion 124 and includes flared or trumpet shaped mouth 129. The inner diameter of chamber member 122 is larger than the outer diameter of PTCA wire 63. Chamber member 122 is connected to shank 76 at connector 130.

Distal portion 124 has rounded concave surface 132 with blunt edges 134, 136 formed by circumferential intersection with substantially linearly shaped longitudinal outer surface 120. Concave surface 132 and trumpet shaped mouth 129 of chamber member 122 allow for greater PTCA wire 63 exploration of occlusion surface 133 (shown in FIGS. 7, 8, and 9). Concave surface 132 and blunt edges 134, 136 are designed to allow balloon member 74 to be advanced to a location substantially directly adjacent (within approximately 0.5 millimeters) of the total occlusion.

Proximal portion 126 has an inflated diameter that is greater than that of distal portion 124. Preferably the surface area of proximal portion 126 is 10–30 percent greater than distal portion 124, with a figure of 20 percent providing excellent results. This structure enables balloon member 74 to exert outward pressure on the muscle wall 131 of coronary artery 34. The larger diameter of proximal portion 126 in conjunction with concave surface 132 and blunt edges 134, 136 of distal portion 124 ensure the formation of cleft 138, while also providing structural braking means for discouraging unwanted retrograde expulsion of balloon member 74.

Figure 3:
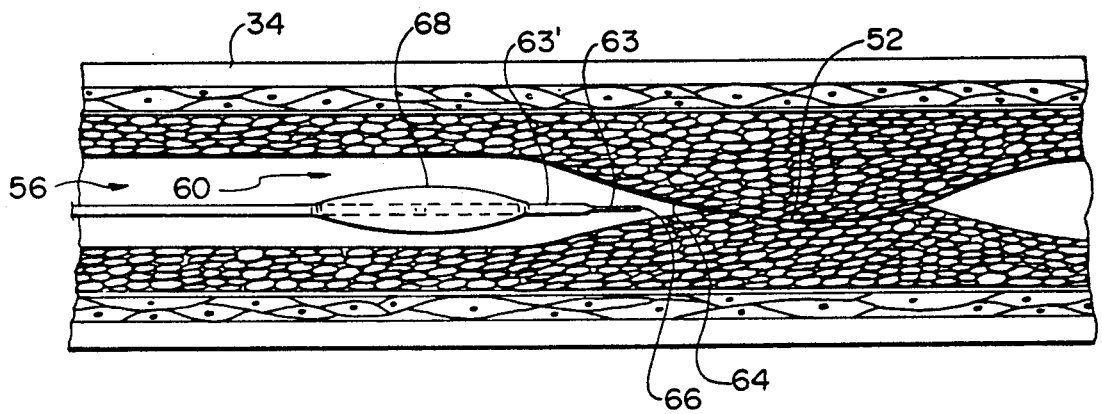
FIG. 3 is a side elevation sectional view of a prior art deflated balloon catheter disposed within a totally occluded artery.
Figure 4:
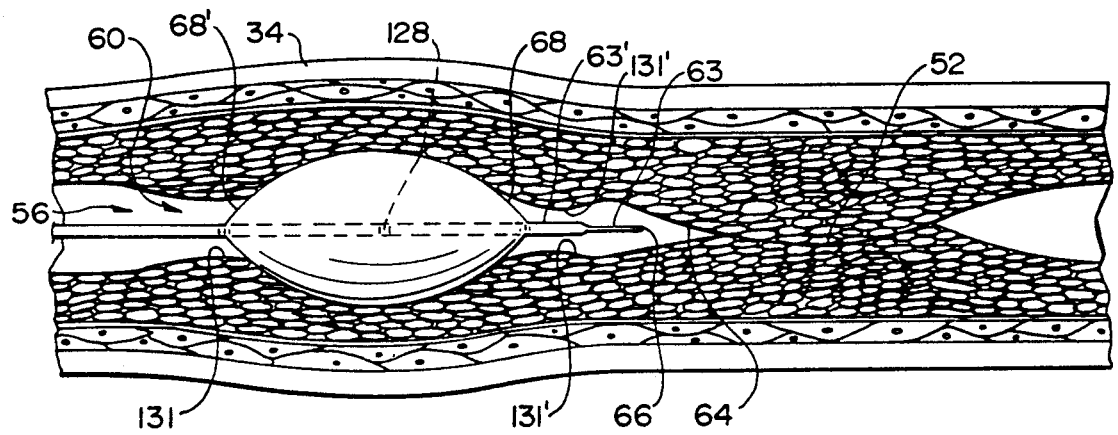
FIG. 4 is a view similar to that of FIG. 3 with the prior art balloon catheter inflated.
Figure 8:
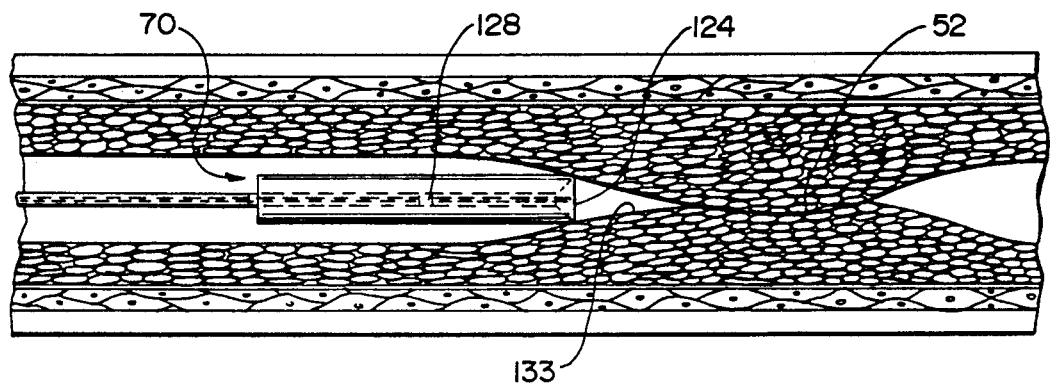
FIG. 8 is a side elevation sectional view of a deflated balloon catheter in accordance with the present invention disposed within a totally occluded artery.
Figure 9:
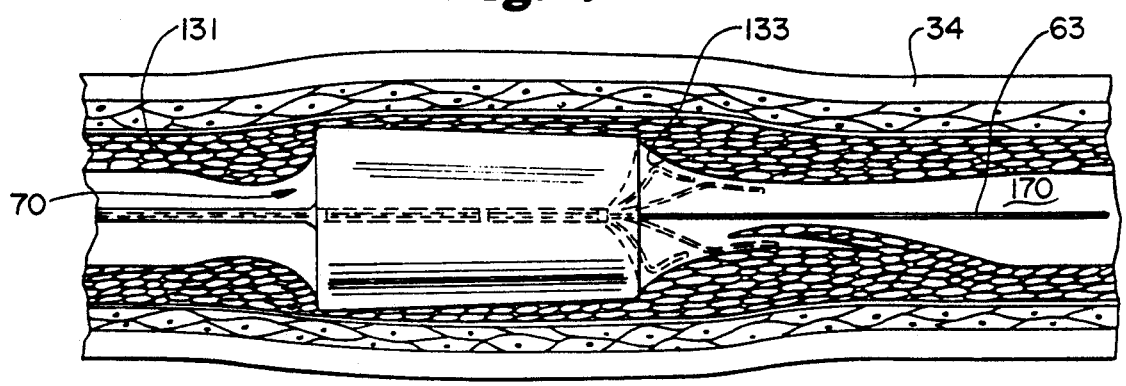
FIG. 9 is a view similar to that of FIG. 8 with the balloon catheter inflated.

FIGS. 2, 3, and 4, disclose common problems experienced with use of conventional PTCA balloon catheters. Such catheters are particularly ill-suited for treatment of resistant chronic total occlusion for several reasons. First, a 3-5 millimeter shaft tip 66 typically extends beyond distal portion 68 of the deflated balloon. This prevents the balloon from entering the most proximal portion of the total occluded artery. Second, prior art balloons are tapered distantly and thereby permit recoil of the arterial wall 131 in the area adjacent to the total occlusion, thus inhibiting or preventing cleft development. Third, the most proximal portion 68' of the balloon is also tapered and when stronger backup is required to advance a PTCA wire across a total occlusion, then expulsion of the balloon proximally has a tendency to occur and may increase the chances of a proximal coronary dissection. Fourth, a standard balloon length of 2 centimeters or greater is frequently longer than the available coronary stump length.

Accordingly, the present balloon catheter 70 invention, shown in FIGS. 1, 5, 6, 7, 8, 9, and 10, solves the problems of prior art devices by several means. First, balloon catheter 70 comprises a blunt distal end portion which provides coronary arterial luminal widening directly adjacent to a total occlusion 52 so that a cleft separation is formed which permits a PTCA wire to be manipulated therethrough, thereby permitting subsequent angioplasty to be performed. Second, balloon catheter 70 provides distal end structure means which permits exit of a PTCA wire from hollow chamber member 122 mouth 129 so that the exit location is further from the occlusion than portions of inflated balloon member 74. This permits improved manipulation of PTCA wire tip 63 to explore and seek out the area of newly formed plaque separation. Third, a preferred balloon member 74 may comprise a balloon member having a size which is short enough to fit a short coronary stump, i.e. approximately less than 2 centimeters. Fourth, retrograde expulsion is limited by providing balloon member proximal portion 128 with a blunt configuration to engage arterial wall 131 in a manner sufficient to discourage such expulsion, as well as to provide further backup support to wire manipulation across a new area of plaque separation.

FIGS. 3, 4, 8, and 9 provide clear illustrations of the operational differences between conventional PTCA wire balloon catheter devices designed for partial coronary stenosis, and the present invention developed specifically for the total occlusion. In FIG. 3, the deflated conventional balloon wire 60 is advanced as close to the total occlusion 52 as possible. The balloon is inflated, but the tapered distal balloon with the shaft tip extension 63' remains at a distance from total occlusion 52. Moreover, the plaqued arterial wall 131' distal to the balloon recoils inward preventing cleft separation. Efforts to mechanically force wire 63 into total occlusion 52 may produce coronary perforation, dissection, or retrograde displacement of the balloon.

In contrast, the present balloon catheter 70 may be advanced to within 0.5 millimeter of total occlusion 52. Then, the blunt and substantially non-tapered distal portion 124, and associated corner portions, provides improved means for cleft formation, improved wire support, and enhanced wire exploration of the entire surface area of the total occlusion until the cleft 170 is entered and crossed.

The invention accordingly consists in the features of the construction, combinations of elements, and construction of parts which will be exemplified in the construction described above and of which the scope of the invention would be indicated in the following claims. It is to be understood that while certain embodiments of the present invention have been illustrated and described, the invention is not to be limited to these specific forms or arrangements of parts herein described and shown.

What is claimed is:

1. A balloon catheter for creating a cleft through a total blockage within a vascular structure presenting an internal vascular wall, comprising:

an elastomeric balloon member having a forward, expandable distal end positionable adjacent said blockage, an opposed, rearward, expandable proximal end, and a generally frustoconical outer balloon surface extending between said proximal end and said distal end, the diameter presented by said outer balloon surface at said proximal end being greater than the diameter presented by said outer balloon surface at said distal surface;

an inner, generally tubular, wire receiving member carried within said balloon member presenting a wire receiving member distal end oriented internally of said outer balloon surface and rearwardly of said balloon member distal end; said balloon member including an outwardly flared mouth surface operably coupling and extending between said wire receiving member distal end and said outer balloon surface at said balloon member distal end; and a rear wall operably coupling and extending between said wire receiving member and said outer balloon surface at said balloon proximal end, the combination of said rear wall intersecting at a functionally acute angle said outer balloon surface at said balloon member proximal end presenting a rearmost balloon member peripheral rim area in engagement with said vascular wall whereby said rim area engages said vascular wall in an angled, biting fit thereby discouraging retrograde expulsion of said balloon member from said blockage.

2. The balloon catheter of claim 1 wherein the balloon member is less than 2 centimeters in length.

3. The balloon catheter of claim 1 wherein the expandable balloon member distal end, when expanded, imparts a radial force against the wall of the vascular structure proximal to the total blockage sufficient to radially expand the wall of the vascular structure surrounding the total blockage to create a cleft through the total blockage.

4. The balloon catheter of claim 1 wherein the expandable distal end is sized for initial non-inflated positioning within 1 millimeter of the total blockage.

5. A balloon catheter for creating a cleft through a total blockage within a vascular structure presenting an internal vascular wall, comprising:

a catheter forwardmost elastomeric balloon member having a blunt, expandable distal end positionable within one millimeter adjacent said total blockage, an opposed, rearward, expandable proximal end portion, and a generally tubular outer balloon surface extending between said proximal end portion and said distal end, the inflated diameters presented by said outer balloon surface at said distal end and said proximal end portion being greater than the normal lumen diameter of said vascular structure;

an inner, generally tubular, wire receiving member carried within said balloon member presenting a wire receiving member distal end oriented internally of said outer balloon surface and rearwardly of said balloon member distal end, and the balloon member including an outwardly flared mouth surface operably coupling and extending between said interventional apparatus receiving member distal end and said outer balloon surface at said balloon member distal end; and said proximal end portion comprising a rear wall operably coupling and extending between said interventional apparatus receiving member and said outer balloon surface, the functionally acutely angled junction of said rear wall and said outer balloon surface forming a rearmost balloon member peripheral rim area in substantial engagement with said vascular wall whereby said rim area engages said vascular wall in a biting fit thereby discouraging retrograde expulsion of said balloon member from the position adjacent said total blockage.

6. The balloon catheter of claim 5 wherein the expandable distal end, when expanded, imparts a radial force against the wall of the vascular structure proximal to the total blockage sufficient to radially expand the wall of the vascular structure surrounding the total blockage to create a cleft through the total blockage.

* * * * *